United States Patent [19]

Broeck et al.

[11] Patent Number: 5,062,858
[45] Date of Patent: Nov. 5, 1991

[54] CONNECTING DEVICE FOR TWO MEMBERS OF AN ARTIFICIAL JOINT

[76] Inventors: Vanden Broeck, 14b route du Curson, CH 1197 Prangins; Olivier De Marchi, Ecole de Duillier, CH 1266 Duillier, both of Switzerland

[21] Appl. No.: 530,312

[22] Filed: May 30, 1990

[30] Foreign Application Priority Data

May 30, 1989 [CH] Switzerland .................. 2023/89

[51] Int. Cl.⁵ .............................................. A61F 2/64
[52] U.S. Cl. ........................................ 623/43; 623/39; 128/80 C; 128/80 F
[58] Field of Search ................... 128/80 C, 80 F; 623/39-46, 38

[56] References Cited

U.S. PATENT DOCUMENTS

| | | | |
|---|---|---|---|
| 4,493,316 | 1/1985 | Reed et al. | 128/80 C |
| 4,726,361 | 2/1988 | Farley | 128/80 F X |
| 4,732,143 | 3/1988 | Kausek et al. | 128/80 F X |
| 4,817,588 | 4/1989 | Bledsoe | 128/80 F X |
| 5,000,169 | 3/1991 | Swicegood et al. | 128/80 C |

FOREIGN PATENT DOCUMENTS

| | | |
|---|---|---|
| 59472 | 9/1982 | European Pat. Off. . |
| 2182714 | 5/1987 | United Kingdom . |

*Primary Examiner*—Randall L. Green
*Assistant Examiner*—David H. Willse
*Attorney, Agent, or Firm*—Cushman, Darby & Cushman

[57] ABSTRACT

Each member of an artificial joint comprises a toothed sector pivoting about a pin. These toothed sectors are in engagement with one another and are mounted between two parallel side plates separated by two spacers. Openings passing through these side plates are angularly distributed about each axis of pivoting and are adapted to selectively receive stops formed by pins which delimit the sectors of freedom of the members about the axes of pivoting. Each of these stops is associated with an apertured tongue which extends perpendicular to the axis of the pin and permits bolting the stop to the center of pivoting of its member.

4 Claims, 1 Drawing Sheet

CONNECTING DEVICE FOR TWO MEMBERS OF AN ARTIFICIAL JOINT

BACKGROUND OF THE INVENTION

1. Field of the Invention

The present invention relates to a pivotal connection or joint device for two members of an artificial joint intended to be attached to respective members for securing the artificial joint to the human body, comprising two supporting side plates fixedly associated with one another and parallel to one another, two pivot pins disposed between these side plates, two semi-circular toothed sectors mounted co-axially on the respective pivot pins, in contact with one another and fixedly associated with the respective members, and adjustable stop means extending into the path of at least one of these members to define its sector of freedom.

Artificial knee joints comprise means of fixation above and below the knee connected to two pivotal connection devices situated on the internal and external parts of the knee.

2. Description of the Prior Art

As is known, the bending-extending movement of the pivotal knee joint occurs by rolling and sliding of the femoral condyles on the articular discs of the tibial plate and not about a fixed center of rotation. This is the reason for the members connecting the fixation members of the artificial joint to the human body not generally being pivoted about a common axis, but about two parallel axes. The two members associated with the same pivotal connection device are kinematically connected, for example by two geared sectors in contact with one another. It is also known to define a sector of freedom for these members by disposing stops in their paths as a function of the bending-extending movement for which limitation of pivoting to that to which the pivotal joint is set is required. This choice is determined by the doctor who must himself carry out on the artificial joint the adjustment of the stops in the paths of the members of the pivotal connection device of the artificial joint.

There exist for this purpose different adjustment systems which have the disadvantage of necessitating tools such as screwdrivers in particular and dismantling and assembly operations with which the doctor is less familiar than the orthopedist.

In particular, there has been proposed in U.S. Pat. No. 4,817,588 such an adjustment system in which the stop members are positioned in notches spaced angularly about the axis of pivoting of an artificial joint, a locking member serving to retain these stop elements in their respective notches. The disadvantage of this adjustment system resides essentially in the fact that it is relatively complex and necessitates therefore the manufacture of quite a large number of components, leading to assembly operations the duration and the difficulty of which are a function of the number of pieces to be put together.

European Patent Specification No. 0,059,472 and U.S. Pat. No. 4,726,361 describe a simpler adjustment system comprising stops disposed along arcuate grooves centered on axes of pivoting and located along these grooves by being secured in position using a screw and a nut disposed one to each side of the plane of the plate in which the groove is formed. The disadvantage of a system of this kind is that the angular position is only defined by the grip of the stops. Taking account of the force which these stops are called upon to withstand by virtue of the length of the arm of the lever, the position of these stops may be accidentally changed.

Another solution proposed in U.S. Pat. No. 4,493,316 comprises two gear wheels carried by arms secured on the axes of pivoting of the two members of the artificial joint, each of which is in engagement with a gear toothing integral with one of these axes, so that these gear wheels are displaced in an angular sense with these gear toothings and limit the angular displacement when they meet the other integral gear toothing of the axis of pivoting of the other member of the artificial Joint. This solution does not enable fixed positions to be determined, these always being a function of a securing operation and thus susceptible to being accidentally displaced.

The same disadvantage is found in British Patent Specification No. 2,182,714A, the angular displacements of the members of the artificial joint being limited by stop screws capable of being dislocated.

As may be confirmed, there does not exist in the state of the art a simple adjustment device capable of defining angles of pivoting in a manner which is incapable of maladjustment, that is to say stop positions which are not dependent upon a simple gripping force. In addition, all of these devices require a specific set of tools not normally available to a medical practitioner.

BRIEF SUMMARY OF THE INVENTION

An object of the present invention is to arrange matters so that this operation of adjustment of the sector of freedom of the members does not necessitate in particular any special tool, nor dismantling of the pivotal connecting device.

Accordingly, the present invention has for its subject a joint device for two members of an artificial joint intended to be associated with respective members for affixing the artificial Joint to the human body, the device comprising two supporting side plates parallel to one another and fixedly associated with one another, two pivot pins disposed between these side plates, two semi-circular toothed sectors mounted co-axially on the respective pivot pins, in engagement with one another and fixedly associated with the respective members, and adjustable stop means extending into the path of at least one of these members to define a sector of freedom for the member, at least one of said side plates comprising positioning openings angularly distributed about the axis of at least one of the pivot pins and two angular stops which are angularly adjustable relative to the axis of this pivot pin, each of these stops comprising a rod extending through a positioning opening of said at least one of said side plates, this rod being integral with a small plate, the plane of which is perpendicular to the longitudinal axis of this rod, and the small plate comprising means for connecting it to the axis of said pivot pin.

BRIEF DESCRIPTION OF THE DRAWINGS

The accompanying drawings illustrate, schematically and by way of example, an embodiment of the joint device which is the subject of the present invention.

DETAILED DESCRIPTION OF THE DRAWINGS

Figure 1:
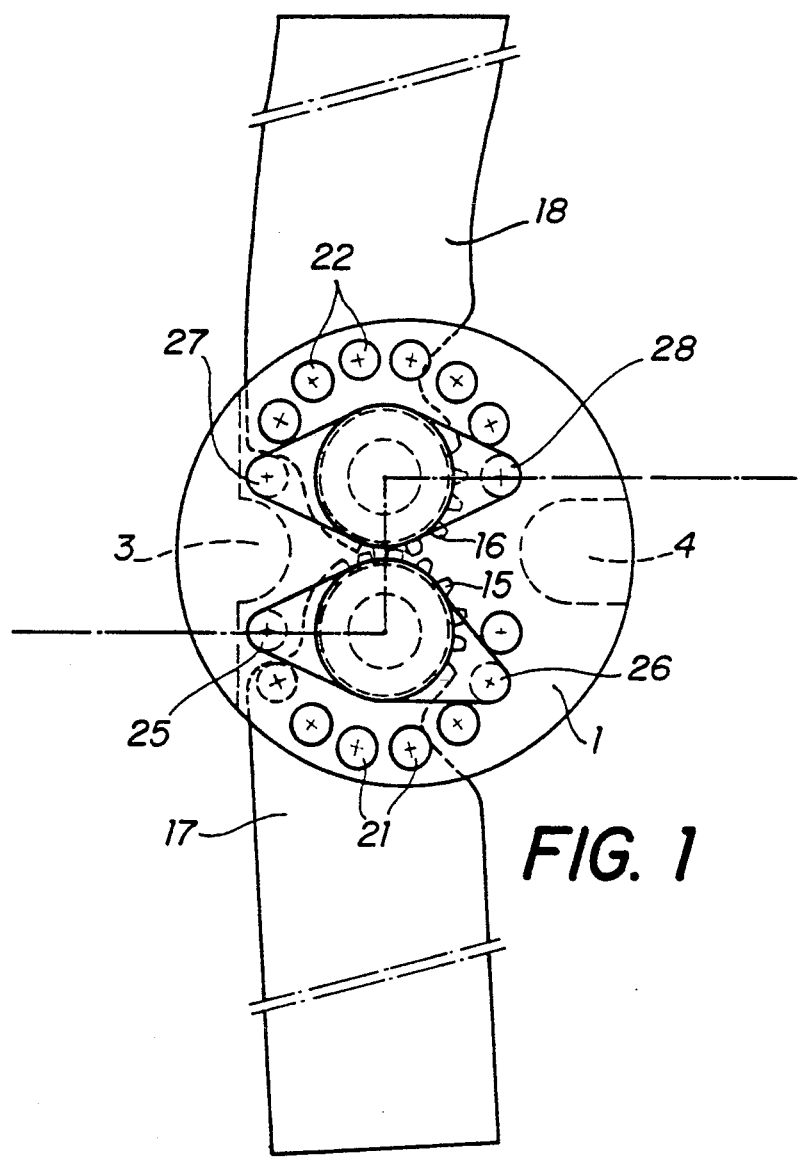
FIG. 1 is a plan view of this device.
Figure 2:
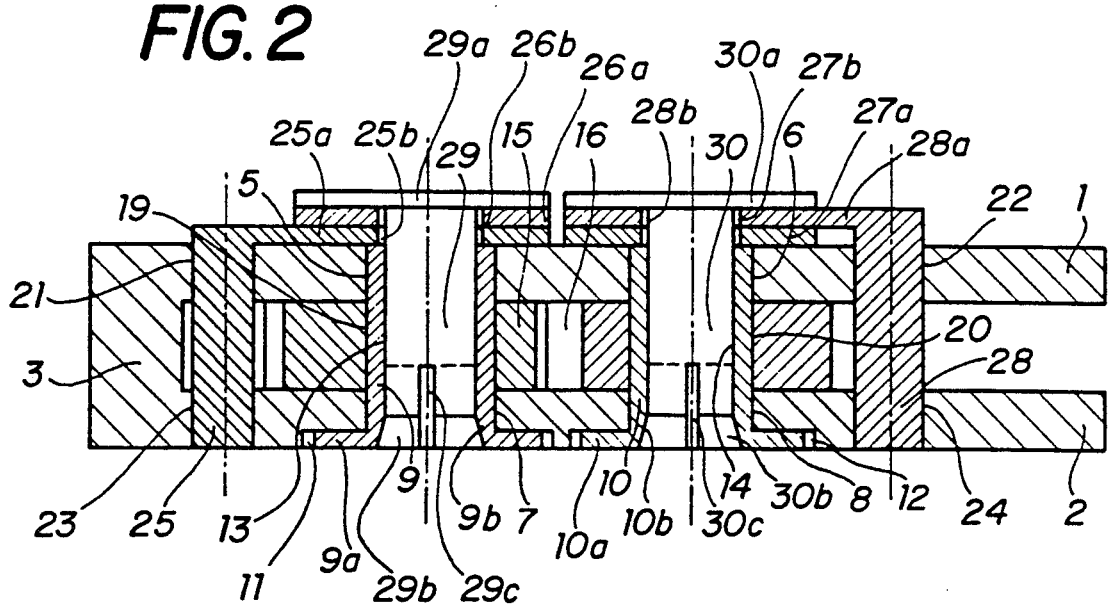
FIG. 2 is a developed sectional view to a larger scale on the line II—II of FIG. 1.

The joint device illustrated by FIGS. 1 and 2 comprises two parallel supporting side plates 1, 2, maintained at a spacing from one another by spacers 3, 4. These side plates and these spacers may advantageously be formed as a single unit by moulding in a plastics material such as polyethylene, for example. These side plates each comprise two openings 5, 6 and 7, 8 respectively, aligned on two respective axes forming two centers of pivotal connection as will be described in the following text.

Two tubular pivot pins 9, 10 are fitted in the two aligned openings 5, 7, and 6, 8 respectively of the two centers of pivoting. Each pivot pin comprises, at one end, an annular flange, 9a, 10a respectively. These flanges engage in recesses 11, 12 respectively, provided in the external surface of the side plate 2 around the openings 7 and 8. The ends of the axial passages 13, 14 of the tubular pivot pins 9, 10, adjacent to the annular flanges 9a, 10a, have conically widening portions 9b, 10b.

Two toothed sectors 15, 16 respectively fixedly associated with the two members 17, 18 intended to be connected to the respective members for attaching the artificial joint to the human body, each comprise an axial opening 19, 20 serving to mount the members 17, 18, which pivot on the tubular pivot pins 9, 10 while maintaining the toothed sectors 15, 16 in contact with one another, so that the two members 17, 18 are kinematically connected to one another.

Each of the openings 5, 6, 7, 8 aligned two by two on the respective axes of the pivot pins 9, 10 is surrounded by positioning openings, respectively 21, 22, 23, 24, angularly distributed on circumferences of the same radii and extending through the respective side plates 1, 2. The openings 21, 22 respectively coincide with the openings 23, 24 respectively, that is to say they have, two by two, respective common axes parallel to the axes of pivoting passing through the centers of the pivot pins 9, 10 respectively.

The adjustable stop means are formed by rods 25, 26, and 27, 28 respectively, which may be introduced into any one pair of positioning openings 21, 23 and 22, 24 respectively.

Each rod 25, 26, 27, 28 is integral at one end with a plate 25a, 26a, 27a, 28a respectively, which extends perpendicular to the longitudinal axis of the rod. Each plate is pierced by an opening 25b, 26b, 27b, 28b for which the distance between its center and the longitudinal axis of the rod corresponds to the radius of the circle on which the openings 21, 22, 23, 24 are distributed about the longitudinal axes of the pivot pins 9, 10. As a consequence, these openings may be brought to coincide with the axial passages 13, 14 of the respective tubular pivot pins 9, 10, when the rods are engaged in the positioning openings.

Each of two securing members is formed by a pin 29, 30 respectively. These pins are engaged in the axial passages 13, 14 respectively of the tubular pivot pins 9, 10 respectively, as well as in the openings 25b, 26b and 27b, 28b respectively of the plates 25a, 26a, 27a, 28a. Each pin 29, 30 has, at one end, a head 29a, 30a which engages against the external plate 25a, 27a respectively, and, at its other end, a tapered part 29b, 30b in which two diametral slots 29c, 30c provide between them four resilient arms. By virtue of this arrangement, the tapered parts 29b, 30b of the pins 29, 30 respectively may grip in the conical tapering portions 9b, 10b respectively, after having passed through the axial passages 13, 14 of the tubular pivot pins 9, 10.

To mount the members 17, 18 on the joint device, it suffices to laterally introduce their toothed sectors 15 and 16 between the side plates 1 and 2 and to make their axial openings 19, 20 coincide with the openings 5, 7 and 6, 8 respectively of the side plates. Each of the tubular pivot pins 9, 10 is then fitted through these openings 5, 7, 19 and 6, 8, 20 respectively. The pivotal connection is, from this moment, in an operational state, but no particular adjustment of the sector in which each member 17, 18 is free to move is set, other than the maximum limits inherent in the construction of the device.

If it is desired to limit, indeed to prevent, the bending-extending movement of the knee to which the artificial joint is to be fixed, the rods 25, 26, and 27, 28 respectively are introduced into the positioning openings 21, 23 and 22, 24 respectively as a function of the angles of extending and of bending desired for this pivotal connection. Given that the two members 17, 18 are kinematically connected to one another, theoretically only one axis of pivoting of one of the pivot pins 9, 10 need be provided with adjustable stop means. However, taking account of the great forces which the device is called upon to withstand, it is necessary that each member be associated with two stops and that these stops be adjustable so that the two members arrive simultaneously against the respective two stops defining the ends of their angular displacements. Once the desired adjustment has been obtained, it suffices to axially introduce the pins 29, 30 of the fixation or securing members into the axial passages 13, 14 respectively of the tubular pivot pins 9, 10 by pushing them until their respective tapered parts 29b, 30b grip in the taperings 9b, 10b of these axial passages.

For the removal of these fixation members, it is only necessary to apply an axial force against the end of the tapered part 29b or 30b. Taking account of the fact that the pivot pins 9, 10 are held in this direction by their annular flanges 9a, 10a and that the tapering portions 9b, 10b are conical, the resilient arms formed by the slots 29c, 30c contract radially towards the center and allow sliding of the pins 29, 30 out of the axial passages 13, 14. To carry out these operations, no particular tool is necessary; any point whatsoever of, for example, a pencil or a scissors is sufficient to extract the fixation members from the axial passages of the pivot pins. While this axial thrust is being exerted on the fixation members, the pivot pins 9, 10 are held by the flanges 9a, 10a. The pivot pins themselves may only be disengaged by exerting an axial thrust on their respective opposite ends. However, this operation is not necessary during adjustment of the degree of freedom of the pivotal connection device. It must however be noted that, by virtue of this arrangement, according to which the fixation members and the pivot pins may be axially removed by axial thrusts exerted in respective opposite directions, the support for the pivotal connection formed by the side plates 1, 2 and the spacers 3, 4 may be formed in one single moulded piece, because the side plates do not have to be separated for the mounting of the members on the pivot pins. This arrangement reduces the number of parts and facilitates the assembly of the pivotal connection which itself does not require any special tool either.

We claim:

1. A joint device for connecting first and second members of an artificial joint, the first and second members being provided to affix the artificial joint to the human body, the joint device comprising:
   first and second supporting side plates disposed in parallel and fixedly coupled to one another;
   first and second pivot pins extending between said first and second side plates;
   first and second semi-circular toothed sectors, one mounted coaxially to each pivot pin, said toothed sectors being in engagement with one another and each being fixedly associated with one of said first and second members; and
   adjustable stop means extending into the path of at least one of said first and second members to define a sector of freedom for said at least one member, at least one of said side plates comprising positioning openings angularly distributed about the axis of at least one of said pivot pins and two angular stops which are angularly adjustable relative to the axis of said at least one pivot pin, each of said stops comprising a rod extending through a positioning opening of said at least one side plate, said rod being integral with a small plate which has a plane perpendicular to a longitudinal axis of said rod, said small plate including means for connecting said small plate to the axis of said at least one pivot pin.

2. A joint device according to claim 1, wherein said at least one pivot pin is traversed by a cylindrical axial opening, one end of which is tapered, said small plate being provided with an opening for coinciding with the other end of said cylindrical axial opening, and a securing member passing through said openings and comprising a pin element provided at one end with a head engaging against said small plate, and, at the other end thereof, with a tapered part corresponding to that of the cylindrical axial opening, two diametral slots providing four radially-extending resilient members in said tapered part of said securing member.

3. A joint device according to claim 2, wherein each said pivot pin comprises a tubular element inserted through two coaxial openings, one in each side plate and comprises a tubular part, having a tapered end, said tapered end being surrounded by an annular axially retaining flange.

4. A joint device according to claim 1, wherein said adjustable stop means extends into a path of each of said first and second members.

* * * * *